United States Patent
Welborn

(10) Patent No.: US 8,523,891 B2
(45) Date of Patent: Sep. 3, 2013

(54) PROBE FOR CARPAL TUNNEL RELEASE TOOL OR TISSUE DISSECTION

(75) Inventor: Kenneth Welborn, Charlottesville, VA (US)

(73) Assignee: MicroAire Surgical Instruments, LLC, Charlottesville, VA (US)

( * ) Notice: Subject to any disclaimer, the term of this patent is extended or adjusted under 35 U.S.C. 154(b) by 265 days.

(21) Appl. No.: 12/710,654

(22) Filed: Feb. 23, 2010

(65) Prior Publication Data

US 2010/0228275 A1    Sep. 9, 2010

Related U.S. Application Data

(60) Provisional application No. 61/154,602, filed on Feb. 23, 2009.

(51) Int. Cl.
   *A61B 17/32*    (2006.01)

(52) U.S. Cl.
   USPC .......................................................... 606/170

(58) Field of Classification Search
   USPC ............................ 604/22, 542; 606/167–180
   See application file for complete search history.

(56) References Cited

U.S. PATENT DOCUMENTS

| 4,834,729 | A | * | 5/1989 | Sjostrom | 606/170 |
| 4,962,770 | A | * | 10/1990 | Agee et al. | 128/898 |
| 4,963,147 | A | * | 10/1990 | Agee et al. | 606/170 |
| 5,306,284 | A | | 4/1994 | Agee et al. | |
| 5,366,465 | A | * | 11/1994 | Mirza | 606/170 |
| 2002/0058884 | A1 | * | 5/2002 | Burbank et al. | 600/564 |
| 2007/0112366 | A1 | | 5/2007 | Welborn et al. | |
| 2008/0119759 | A1 | * | 5/2008 | McLain | 600/567 |

* cited by examiner

*Primary Examiner* — Ryan Severson
*Assistant Examiner* — Ashley Fishback
(74) *Attorney, Agent, or Firm* — Whitham Curtis Christofferson & Cook, PC

(57) ABSTRACT

A probe for a surgical instrument used for cutting selected tissue in a body cavity while under visual inspection, e.g., a surgical tool for the release of the transverse carpal tunnel ligament, has a profile where the flat top surface of the probe has a wider width dimension than the lower surface of the probe. Thus, the sides of the lower surface are sloped or curved inward such that all points below the flat top surface at any particular point on the first and second sides of the flat top surface have a width that is smaller than the width dimension of the flat top surface. The degree of sloping or curving inward will cause tissues to be moved downward (instead of upward) when the probe is inserted, and will provide for generating an upward force that firmly holds the probe against the tissue to be cut and a downward force on the surrounding tissue below the probe.

9 Claims, 1 Drawing Sheet

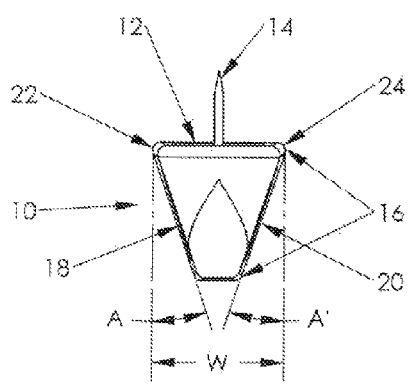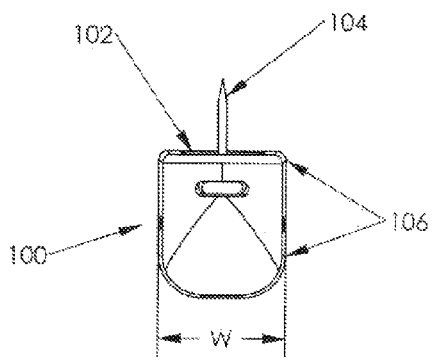
FIGURE 1a  FIGURE 1b - PRIOR ART
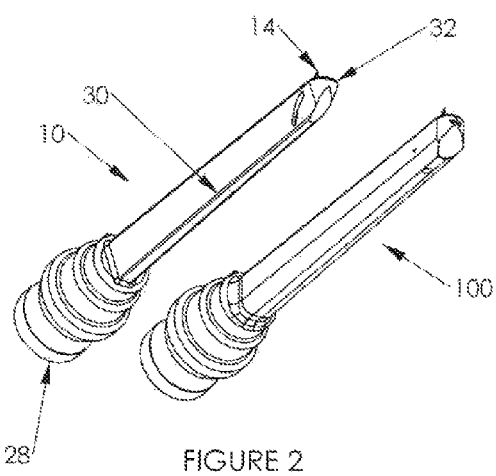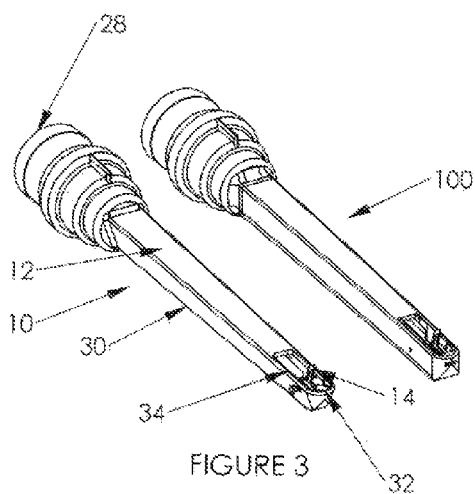
FIGURE 2  FIGURE 3
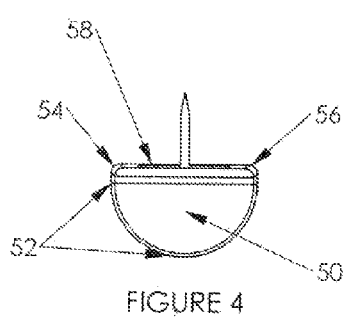
FIGURE 4

PROBE FOR CARPAL TUNNEL RELEASE TOOL OR TISSUE DISSECTION

This application claims priority to U.S. provisional patent application 61/154,602 filed Feb. 23, 2009, and the complete contents thereof is herein incorporated by reference.

BACKGROUND

MicroAire Surgical Instruments has been marketing for a number of years a surgical tool based on U.S. Pat. No. 4,962,770 to Agee et al., U.S. Pat. No. 4,963,147 to Agee et al., U.S. Pat. No. 5,089,000 to Agee et al., and U.S. Pat. No. 5,306,284 to Agee et al, each of which is incorporated fully herein by reference. Recent modifications on the Agee designed hand piece are described in U.S. Pat. No. 7,628,798 to Welborn which is incorporated fully herein by reference. This surgical tool is used to inspect and manipulate selected tissue in a body cavity, and has particular application to performing safe and effective carpal tunnel release. These tools include a handle assembly, a probe member, an optical system, and a cutting system. The optical system and cutting system extend through the handle and into the probe and permit a surgical blade to be selectively deployed and retracted from a lateral opening in the top surface of the probe at its distal end.

The preferred use of the surgical instrument in performing carpal tunnel release is accomplished by forming a short transverse incision located proximal to the carpal tunnel and the wrist flexion crease. After longitudinal spreading dissection, to avoid injury to the sensory nerves, the incision is continued through the deep fascia of the forearm, the distal extension of which leads to the flexor retinaculum. After an incision through the finger flexor synovium, extension of the wrist will then expose the proximal opening of the carpal tunnel, thereby forming a passage to the carpal tunnel. In the Agee designed tool, the rotational orientation of the probe relative to the handle or holder is adjustable to suit the needs of the surgeon. After adjusting the rotational orientation of the probe, the probe is inserted through the incision and desirably through the length of the carpal tunnel to the distal edge of the transverse carpal ligament.

By employing the optical system, and through manipulation of the patient's extremities, the anatomy within the carpal tunnel can be clearly visualized on a display of a video monitor connected to a video camera and lighting source associated with the optical system. The distal end of probe will desirably have gently displaced the tendons, bursa and median nerve found within the carpal tunnel to facilitate insertion of the probe. Then the lateral aperture of the probe will be positioned adjacent the surface of the flexor retinaculum and, desirably, the configuration of the probe upper surface (which is preferably a flat surface) will exclude the displaced tissues from the region surrounding the lateral aperture. Markers can be used to indicate the point on the probe where the blade elevates, and help facilitate proper placement of the probe relative to the distal edge of the flexor retinaculum.

At the appropriate location, a cutting blade will be extended to contact the distal edge of the flexor retinaculum, while the surgeon views the tissue to be divided via the display. The blade point will desirably be extended to a position sufficient to completely release the ligament. While viewing (through the lateral aperture in the probe) the intended path of the extended cutting blade, the probe is then withdrawn, thereby dividing the flexor retinaculum and releasing the carpal tunnel.

The surgical tool described by Agee et al. is safe and effective and well regarded in the surgical community. Improvements to the probe design to enhance safety during the cutting procedure will be well received.

SUMMARY

In an embodiment of the invention, a probe for a surgical instrument used for cutting selected tissue in a body cavity while under visual inspection, e.g., a surgical tool for the release of the transverse carpal tunnel ligament, has a flat top surface with an adjoining semicircular lower surface.

In an embodiment of the invention, a probe for a surgical instrument used for cutting selected tissue in a body cavity while under visual inspection, e.g., a surgical tool for the release of the transverse carpal tunnel ligament, has a flat top surface with an adjoining lower surface which has inwardly sloped sides where a slope of each side beginning at the sides of the flat top surface is greater than or equal to a 5, 10, 20, or 30° angle inward from a vertical line passing through the sides of said flat top surface.

According to the invention, a probe with a triangular or trapezoidal profile (or any other polygonal profile) or with a semicircular profile (i.e., a half of a circle where the arc measures) 180°), where the lower surface at all points below the flat top surface has a width which is less than the width dimension of the flat top surface provides a number of safety advantages. For example, the sloped or semicircular sides can provide the advantage of excluding tissue from the blade cutting path; the probe will have a smaller displacement volume which will reduce neuropraxia; and the sloped or semicircular sides help produce in a reaction force within the body that causes the cutting probe to be held against the transverse carpal ligament.

The probe of this invention is used on surgical instruments that are designed for cutting selected tissue in a body cavity while under visual inspection. Particular examples of such surgical instruments are those that are used for releasing the transverse carpal ligament. The probe includes a proximal end connected to or connectable to a surgical hand piece. That is, in some cases the probe will be separable from the hand piece and will be a disposable item. However, in some instances, the probe can be permanently connected to the hand piece, with, for example, the handpiece and probe being disposable. The proximal end of the probe is open so as to allow passage of optical system and a cutting tool extension system into the probe. A hollow length extends from the proximal end to a closed distal end of the probe. The hollow length has a flat top surface with a lateral aperture near the distal end (i.e., relatively closer to the distal end than the proximal end and preferably within a few millimeters or centimeters of the distal end). A cutting blade can be extended and retracted through the lateral aperture under operation of a cutting tool extension system while visualizing tissue at the lateral aperture with the optical system. The flat top surface has a width dimension spanning a distance from a first side to a second side. This width dimension can remain constant for the entire length of the probe or can vary slightly (e.g., relatively larger near the proximal end and relatively smaller near the distal end). A lower surface connected to the first side and the second side of said flat top surface is sized to permit passage of an optical system and a cutting tool extension system between said flat top surface and said lower surface. The lower surface can be either semi-circular in cross-section or have sloped side walls (e.g., triangular, trapezoidal or polygonal in cross-section. In the case of having sloped sides, the slope of each side beginning at the first and second sides of the flat top surface is greater than or equal to a 5 degree angle inward from a vertical line passing through the first and second sides of the flat top surface. The profile is such that the lower surface at all points below said flat top surface at the first and second sides has a width which is less than said width dimension of the flat top surface.

DESCRIPTION OF THE DRAWINGS

FIGS. 1a and 1b respectively show a triangular (or trapezoidal) profile embodiment of a probe, and the prior art non-sloped design of a probe;

FIG. 2 shows side-by-side isometric bottom views of triangular (or trapezoidal) profile embodiment of a probe, and the prior art non-sloped design of a probe;

FIG. 3 shows side-by-side isometric top views of triangular (or trapezoidal) profile embodiment of a probe, and the prior art non-sloped design of a probe; and FIG. 4 shows a semicircular profile embodiment of a probe.

DETAILED DESCRIPTION

The invention is to provide an improved probe for a surgical instrument used for cutting selected tissue in a body cavity while under visual inspection, such as carpal tunnel release tool which is described in U.S. Pat. Nos. 4,926,770, 4,963,147, 5,089,000, 5,306,284, and 7,628,798, each of which are herein incorporated by reference. In particular, the invention pertains to the profile of the probe and particularly contemplates a profile where the flat top surface of the probe has a wider width dimension than the lower surface of the probe. That is, the sides of the lower surface are sloped or curved inward such that all points below the flat top surface at any particular point on the first and second sides of the flat top surface have a width that is smaller than the width dimension of the flat top surface. The degree of slope is such that it can provide the advantage of excluding tissue from the blade cutting path. The probe with inwardly sloped or curved sides on its lower surface will have a smaller displacement volume which will reduce neuropraxia. Further, the sloped or semicircular sides are configured to help produce in a reaction force within the body that causes the cutting probe to be held against the transverse carpal ligament.

One advantage of the profile is that while the top of the probe remains horizontal, the sides will slope down to the bottom which will cause tissues in the carpal tunnel to be moved downward, away from the blade. During dissection of the transverse carpal tunnel ligament, it is not uncommon for tissue, such as the median nerve and tendon to slide over the top of the probe into the path of the blade. Cutting the median nerve and tendon is not desirable. Having inwardly sloped or curved sides will make the tissue more like to move downward when the probe is inserted and in place instead of into the blade path, thereby increasing the safety and efficacy of the procedure.

Another advantage of the profile is that it enables the probe to have less volume while keeping the top surface at a desired width dimension (e.g., 1 tp 15 millimeters). The top surface of the probe has several important features that make it safe and effective for releasing the transverse carpal ligament. For example, the flat top feature allows the instrument to be applied directly to the underside of the transverse carpal ligament which excludes tissues from the field of view and the path of the blade. Further, the width of the flat top surface requires the excluded tissue to remain a fixed distance from the blade. The profile for the probe contemplated herein retains the advantages of the flat top surface while at the same time reducing the volume displaced by the probe. This safety feature is important for avoiding nerve compression syndrome. By reducing the displacement volume of the probe, the new probe profile decreases the chance of neuropraxia.

A further advantage of the profile is that the inwardly sloped or curved sides allows for the compressive forces in the carpal tunnel to be used to hold the cutting probe firmly against the transverse carpal ligament (or other tissue which is to be cut). The inwardly sloped or curved sides provide the advantage of creating a vertical reaction force that pushes the probe against the transverse carpal ligament (or other tissue to be cut). This excludes tissue from the blade path and increases safety and efficacy of the procedure.

FIG. 1a shows an end view of a probe 10 according to one embodiment of the invention. The probe 10 can be considered as having a triangular or trapezoidal profile.

FIG. 1b shows an end view of a probe 100 used in the prior art. The probe 100 can be considered as having a generally rectangular profile.

The probes 10 and 100 respectively have a flat top surface 12 and 102 which has the same width dimension "W". Preferably, the width W ranges between 0.1 and 1.5 centimeters. The flat top surface 12 and 102 functions to keep the probe 10 and 100 flat against the tissue which is to be cut. Also, the width W functions to space the cutting blade 14 or 104 away from tissue which is desirable not to cut.

The important difference between the probe 10 and probe 100 is the profile which is achieved when a different lower surface 16 or 106 is employed. In FIG. 1a, the profile could be considered triangular or trapezoidal, while in FIG. 1b, the profile could be considered rectangular. In the embodiment shown in FIG. 1a, the lower surface 16 has sloped sides 18 and 20. The slope of each side 18 and 20 beginning at the first and second sides 22 and 24 of the flat top surface 12 is greater than or equal to a 5°, a 10°, a 20°, or a 30° angle inward from a vertical line passing through the first and second sides of the flat top surface as denoted by angles A and A'. Thus, the profile of the probe 10 is such that the lower surface 16 at all points below the flat top surface 12 at the first and second sides 22 and 24 has a width which is less than the width dimension of the flat top surface 12. This profile both pushes tissue surrounding the probe 16 downward, and, when in place, the surrounding tissue pushes the probe 16 upward. This assures that the flat top surface 12 is held firmly against the tissue to be cut, and prevents other tissues (e.g., the tendons, bursa, nerves, etc. such as those found within the carpal tunnel) from slipping above the probe 16 and into the path of the cutting blade 14.

In contrast, in FIG. 1b, with a generally rectangular profile for the probe 100, the profile of the probe 100 does not exert a downward push on surrounding tissue, and the surrounding tissue cannot exert an upward push on the probe 100. In some molding operations the generally rectangular shape of the probe 100 may have a slightly wider top surface 102 than the sidewalls of the lower surface 106 (e.g., a slope of 2° or less); however, this slight amount of sloping is not sufficient to provide the enhanced safety features attributable to the inventive profile because there is insufficient slope for downward and outward movement of the surrounding tissue and insufficient slope for an upward reaction force for the surrounding tissue to impart to the probe.

Furthermore, the profile of probe 16 provides for a significantly smaller displacement than occurs with the profile of probe 106, which aids in reducing compression related injuries.

FIGS. 2 and 3 show side-by-side isometric views of the probe 10 and the probe 100, particularly as adapted for use on a surgical tool used for releasing the transverse carpal ligament. In general, it is proposed to have the probe 10 be similar to the probe 100 in most respects so that it can function as a substitute on currently available carpal tunnel release tools, such as those which are available from MicroAire Surgical Instruments of Charlottesville, Va. That is, the probe 10 may be made of a plastic material, but may also be made of materials such as composites, glass and metal. The probe 10 will be hollow and will have a proximal end 28 connected to or connectable to a surgical handpiece where the proximal end is open so as to allow passage of optical system and a cutting tool extension system (not shown). The probe 10 will have a hollow length 30 that extends to a closed distal end 32. The length of the hollow length 30 can vary and will typically range from 3 to 15 centimeters. The flat top 12 of the probe 10 will have an aperture 34 near its distal end 32. The aperture 34 will allow a cutting blade 14 to be selectively extended and retracted from the probe 10, and will allow an optical system which passes through the probe 10 to image the tissue above the aperture 34. Thus, the probe 10 permits the surgeon to move the probe within a body cavity while under visual inspection, and then to selectively deploy a cutting blade 14 from the aperture 34 to cut desired tissues (e.g., the transverse carpal ligament).

While FIG. 1a shows the profile of the probe as being a triangular or trapezoidal, it should be understood that other polygonal configurations could be used so long as the lower surface remains of a smaller width at all points below the side edges of the top surface.

FIG. 4 shows a variation on this concept where the profile of the probe 50 is semicircular. That is the lower portion 52 has an arc of 180° beginning at the left and right sides 54 and 56 of the probe 50. As the lower portion 52 is semicircular, it immediately begins to slope away from the edges 54 and 56 of the top surface 58 of probe 50, in contrast to the lower portion 106 of probe 100 shown in FIG. 1b. This assures that the flat top surface 58 is held firmly against the tissue to be cut, and prevents other tissues (e.g., the tendons, bursa, nerves, etc. such as those found within the carpal tunnel) from slipping above the probe 50 and into the path of the cutting blade 14.

While the invention has been described in terms of its preferred embodiments, those skilled in the art will recognize that the invention can be practiced with modification within the spirit and scope of the appended claims.

The invention claimed is:

1. A probe for a surgical instrument used for cutting selected tissue in a body cavity while under visual inspection, said probe comprising:
   a proximal end connectable to a surgical handpiece, said proximal end being open so as to allow passage of optical system and a cutting tool extension system;
   a distal end, said distal end being closed; and
   a hollow length extending from said proximal end to said distal end, said hollow length having
      a flat top surface with a lateral aperture near said distal end through which a cutting blade can be extended and retracted under operation of the cutting tool extension system while visualizing tissue at said lateral aperture with said optical system,
      said flat top surface having a width dimension spanning a distance from a first side to a second side of said flat top surface, and
      a lower surface connected to said first side and said second side of said flat top surface, said lower surface being sized to permit a passage of an optical system and a cutting tool extension system between said flat top surface and said lower surface,
   said lower surface either
      i) being semi-circular in cross-section having an arc measuring 180 degrees, or
      ii) having sloped sides where a slope of each side beginning at said first and second sides of said flat top surface is greater than or equal to a 5 degree angle inward from a vertical line passing through said first and second sides of said flat top surface,
   wherein said lower surface at all points below said flat top surface at said first and second sides has a width which is less than said width dimension of said flat top surface.

2. The probe of claim 1 wherein said lower surface of said hollow length is semi-circular in cross-section.

3. The probe of claim 1 wherein said lower surface of said hollow length is triangular or trapezoidal in cross-section.

4. The probe of claim 1 wherein said lower surface of said hollow length has sloped sides where a slope of each side beginning at said first and second sides of said flat top surface is greater than or equal to a 10 degree angle inward from a vertical line passing through said first and second sides of said flat top surface.

5. The probe of claim 1 wherein said lower surface of said hollow length has sloped sides where a slope of each side beginning at said first and second sides of said flat top surface is greater than or equal to a 20 degree angle inward from a vertical line passing through said first and second sides of said flat top surface.

6. The probe of claim 1 wherein said probe is constructed from plastic.

7. The probe of claim 1 wherein said hollow length has a length dimension which ranges from 3 to 15 centimeters.

8. The probe of claim 1 wherein said width dimension of said flat top surface ranges from 0.1 to 1.5 centimeters.

9. A probe for a surgical instrument used for cutting selected tissue in a body cavity while under visual inspection, said probe comprising:
   a proximal end connected to or connectable to a surgical handpiece, said proximal end being open so as to allow passage of optical system and a cutting tool extension system;
   a distal end, said distal end being closed; and
   a hollow length extending from said proximal end to said distal end, said hollow length having
      a flat top surface with a lateral aperture near said distal end through which a cutting blade can be extended and retracted under operation of the cutting tool extension system while visualizing tissue at said lateral aperture with said optical system,
      said flat top surface having a width dimension spanning a distance from a first side to a second side of said flat top surface, and
      a lower surface connected to said first side and said second side of said flat top surface, said lower surface being sized to permit a passage of an optical system and a cutting tool extension system between said flat top surface and said lower surface,
   said lower surface has sloped sides where a slope of each side beginning at said first and second sides of said flat top surface is greater than or equal to a 5 degree angle inward from a vertical line passing through said first and second sides of said flat top surface,
   wherein said lower surface at all points below said flat top surface at said first and second sides has a width which is less than said width dimension of said flat top surface.

* * * * *